(12) United States Patent (10) Patent No.: US 8,743,356 B1
Mathieu et al. (45) Date of Patent: Jun. 3, 2014

(54) MAN-PORTABLE DEVICE FOR DETECTING HAZARDOUS MATERIAL

(71) Applicant: Her Majesty the Queen in Right of Canada, as represented by the Minister of National Defence, Ottawa (CA)

(72) Inventors: Pierre Mathieu, Quebec (CA); Pierre Lahaie, Quebec (CA); Jean-Robert Simard, Quebec (CA); Sylvie Buteau, Quebec (CA); Denis Nadeau, Quebec (CA)

(73) Assignee: Her Majesty the Queen in right of Canada as represented by the Minister of National Defence, Ottawa, ON (CA)

( * ) Notice: Subject to any disclaimer, the term of this patent is extended or adjusted under 35 U.S.C. 154(b) by 0 days.

(21) Appl. No.: 13/684,219

(22) Filed: Nov. 22, 2012

(51) Int. Cl.
G01J 3/00 (2006.01)
G01N 21/00 (2006.01)
G01N 21/55 (2014.01)

(52) U.S. Cl.
CPC ................................. *G01N 21/553* (2013.01)
USPC ........................................... 356/51; 356/445

(58) Field of Classification Search
CPC .................................................. G01N 21/553
USPC ............................ 356/51, 445–448, 300–334
See application file for complete search history.

(56) References Cited

U.S. PATENT DOCUMENTS

| | | |
|---|---|---|
| 4,365,153 A | 12/1982 | Seigel et al. |
| 5,412,219 A | 5/1995 | Chappelle et al. |
| 5,474,910 A | 12/1995 | Alfano |
| 6,272,376 B1 | 8/2001 | Marcu et al. |
| 6,377,346 B1 * | 4/2002 | Vaisala et al. ................. 356/417 |
| 6,690,463 B2 | 2/2004 | Kask |
| 7,015,484 B2 | 3/2006 | Gillispie et al. |
| 7,103,402 B2 * | 9/2006 | Vo-Dinh ....................... 600/476 |
| 7,154,102 B2 | 12/2006 | Poteet et al. |
| 7,525,102 B1 | 4/2009 | Henshaw et al. |
| 7,573,570 B2 | 8/2009 | Zhang |
| 7,821,633 B2 | 10/2010 | Jalali et al. |
| 8,190,242 B2 | 5/2012 | Demos et al. |
| 2007/0165875 A1 | 7/2007 | Rezvani et al. |

(Continued)

OTHER PUBLICATIONS

R.F. Chen et al., The Application of Time-Resolved Spectrofluorometry to Measuring Benthic Fluxes of Organic Compounds, Org. Geochem, vol. 26, No. 1/2, pp. 67-77, 1997.

(Continued)

*Primary Examiner* — Michael P Stafira
(74) *Attorney, Agent, or Firm* — Marks & Clerk; Richard J. Mitchell

(57) ABSTRACT

A man portable device for detecting the presence of hazardous material includes a pulsed or time-modulated light source and an objective scannable across the surface of a sample for projecting light from the light source onto a succession of spots on the surface of the sample. A spectrometer performs a spectral analysis of the induced fluorescence to create a first dataset defining a first vector as a function of wavelength. A time domain detector for measuring the time decay of the induced fluorescence collected simultaneously creates a second dataset defining a second vector as a function of time. A computer identifies hazardous material by performing independent multivariate analysis on the first and second vectors as the objective is scanned across the sample surface based on fluorescent signal models for hazardous materials in the spectral and time domains.

29 Claims, 2 Drawing Sheets

(56) References Cited

U.S. PATENT DOCUMENTS

2007/0168412 A1   7/2007   Devaul
2009/0219524 A1*  9/2009   Wang et al. .................. 356/301
2011/0101241 A1   5/2011   Cottier et al.
2012/0038908 A1   2/2012   Beckstead et al.

OTHER PUBLICATIONS

Hugo Lavoie et al., LWIR Hyperspectral Imaging for Clandestine Laboratory Detection, Pub Ref Nbr (e.g. RTO-MP-IST-999), Paper Nbr—1.

* cited by examiner

MAN-PORTABLE DEVICE FOR DETECTING HAZARDOUS MATERIAL

FIELD OF THE INVENTION

This invention relates to the field of hazardous material detection, and in particular to a portable for detecting the presence of hazardous material, such as Chemical, Biological, Radioactive, Nuclear, Explosive (CNBRE) material in the field.

BACKGROUND OF THE INVENTION

Current practice in the field for the detection of very low concentrations of threatening CBRNE surface contaminants is to sweep the target surface with a special cloth known to be free of all CBRNE traces. Once the targeted surface has been swept, the cloth is placed in a sealed container for subsequent (bio-) chemistry analysis. Only one surface is swept with a given cloth to avoid dilution of the sample material. The (bio-) chemistry procedures for a given sample may take several minutes up to several days depending on the complexity of the analysis process. These (bio-) chemistry procedures have the advantage of providing various depth of information (usually correlated with the time and complexity of the executed procedure) on the sampled material that can be tailored to the objectives of the CBRNE contamination survey (presumptive detection up to forensic investigation).

There are two major limitations associated with the physical sampling of a given surface with a dedicated cloth and a subsequent timely demanding (bio-) chemistry procedure in assessing the presence of very low concentration of CBRNE contaminants. First, investigating a CBRNE crisis event at a given location involves blindly sampling numerous surfaces for the presence of contaminants. Each sample requires a single cloth and a subsequent (bio-) chemistry procedure. In some cases where the nature of the CBRNE event is unknown, multiple (bio-) chemistry procedures may be performed from a single sample. This blind investigation requires important man-powered efforts, a sizeable equipment infrastructure and a non negligible quantity of consumables while usually only a very small fraction of the processed samples will disclose the presence of CBRNE contaminants. Second, a non-negligible delay is unavoidable between the sampling procedure and the outcomes of the (bio-) chemistry analyses. This delay may result in a delay in taking important decisions concerning the rapid initiation of efficient protection measures, the adequate delimitation of the prohibited areas and the quick selection of adequate medical countermeasures.

US patent publication no. 2012/0038908 discloses a system for detecting CNBRE hazards using fluorescence and spectroscopic imaging techniques wherein data sets generating during interrogation are compared to a reference database. However, a problem is that each specimen may contain several tens of thousands of samples acquired within a few seconds, and producing a rapid response can be a serious challenge.

U.S. Pat. No. 6,272,376 discloses the use of time-resolved, laser-induced fluorescence spectroscopy in the identification of tissue.

U.S. Pat. No. 7,821,633 discloses an apparatus for performing Raman spectroscopy with time domain spectral analysis.

U.S. Pat. No. 8,190,242 discloses a laser synthesizer for multi-dimensional spectroscopy.

SUMMARY OF THE INVENTION

Embodiments of the invention provide a tool for the First Responders to identify rapidly the most promising surfaces that may present CBRNE contaminants, to reduce greatly the number of surfaces where physical sampling is performed and the subsequent (bio-) chemistry procedures, and to provide within seconds a level of classification of the detected CBRNE contaminants allowing the immediate selection of adequate protective measures.

The invention combines time-resolved spectrofluorimetry and multi-variate statistical analysis in a single field instrument well adapted to First Responders Operating Concepts when having to investigate for the presence of very low concentration CBRNE surface contaminants at a reported crisis site.

According to the present invention there is provided a man portable device for detecting the presence of hazardous material, comprising: a pulsed or time-modulated light source; an objective scannable across the surface of a sample for projecting light from the light source onto a succession of spots on the surface of the sample to induce fluorescence; a spectrometer for performing a spectral analysis of the induced fluorescence to create a first dataset defining a first vector as a function of wavelength; a time domain detector for measuring the time decay of the induced fluorescence to create a second dataset defining a second vector as a function of time; and a computer configured to identify hazardous material by performing independent multivariate analysis on the first and second vectors as the objective is scanned across the sample surface based on fluorescent signal models for hazardous materials in the spectral and time domains.

The fluorescent signal models may be stored in memory and based on theoretical or experimental data or a combination of the two.

The combination of spectrally-resolved UV light induced fluorescence and time-resolved fluorescence decay resulting from probing statistically independent tiny areas part of the inspected surface, is used to detect, classify and quantify very small concentration of fluorescing CBRNE surface contaminants.

In order to minimize the clutter generated by background surfaces and to address the sparse distribution of micron size contaminants on these surfaces, the instrument sweeps a targeted surface using dedicated spacers and fires a series of light pulses on areas of this surface ranging from a few to a few tens of microns in size. The manual sweeping speed, size of the irradiated areas and frequency of the light pulses are adjusted to probe a different area with each pulses. Through a single sweep, an ensemble of tens, if not hundreds of thousands of spots or areas is probed. The spectrally and time resolved light induced fluorescence (LIF) associated with each areas are analyzed with a multi-variate algorithm. Based on a library containing the LIF spectral and temporal characteristics of multiple products of interest, the detection/classification of the compounds among the end-members of this library as well as the quantification of their concentrations on the probed surface are derived from the multi-variate analysis of this ensemble. This detection/classification/quantification results are communicated within seconds to the First Responders through a simple small electronic display.

BRIEF DESCRIPTION OF THE DRAWINGS

The invention will now be described in more detail, by way of example only, with reference to the accompanying drawings, in which:—

DETAILED DESCRIPTION OF THE INVENTION

Figure 1:
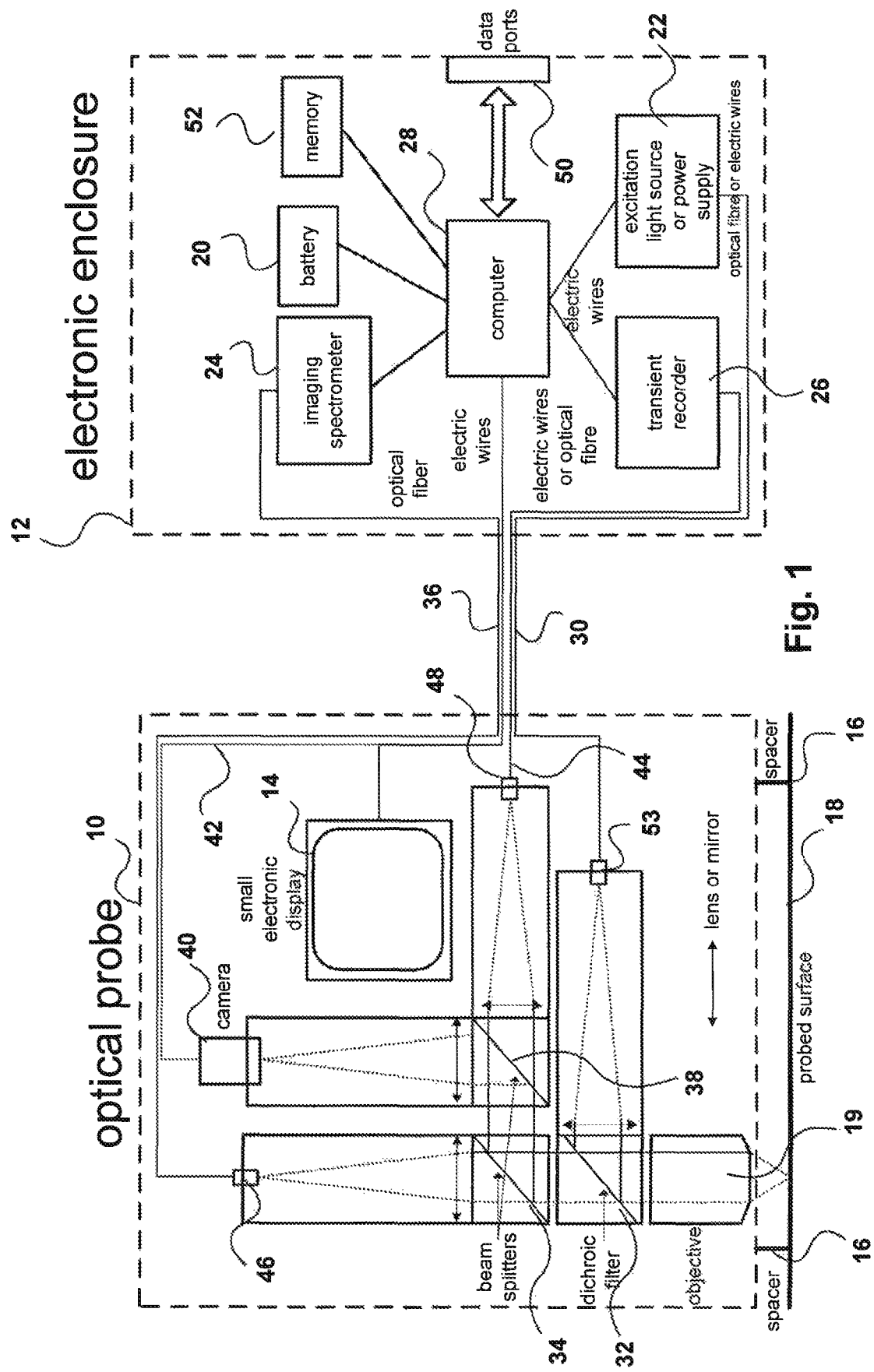
FIG. 1 is a block diagram of a man-portable device in accordance with an embodiment of the invention.

As shown in FIG. 1, the instrument is composed of two main hardware components: the optical probe 10 and the electronic enclosure 12, the two being linked with optical fibers and low power electric wires.

The optical probe 10 includes the optical multiplexing assembly, which may include cube beamsplitters, semi-transparent mirrors, dichroic mirrors, dichroic beamsplitters, volume Bragg grating and holographic beam samplers as well as intermediate lens and optical filters as shown in FIG. 1. The optical multiplexing assembly combines and separates the different optical signals going through the objective. It routes the excitation light pulses toward the surface under investigation and the returned fluorescence or reflected imaging light to the spectrometer 24 (via optical fiber 36), the transient detector 48, and the camera 40.

A simple small electronic display 14 is located on the optical probe 10 and the combined component is ergonomically designed as a pen-like probe to be manipulated as a large pen. A dedicated spacer 16, based on ball bearing or an equivalent technology facilitating the sweeping process, is in contact with the probed surface 18 and keeps approximately constant the distance between the pen's optical port and the probed surface during the sweep. Special care is applied to the design of this spacer component 16 to eliminate all possible subsequent contaminations between sweeps or after the investigation process.

The electronic enclosure contains a battery 20, an excitation light source 22 (if not integrated to the optical probe), the imaging spectrometer 24, the high speed transient recorder electronics 26 as well as the computing components 28 controlling the instruments, recording the collected information, executing the multi-variate program analysis over the ensembles of collected data, presenting the results on the small electronic display 14 and controlling specialized data communication through electronic data ports 50. The computer 28 is connected to a memory 52 storing a library of spectral and time domain signatures based on models for hazardous materials in the spectral and time domains. The electronic enclosure 12 is sufficiently small and low weight to be located in a man-portable packsack and can be operated for a few hours without recharging the battery.

The excitation light from source 22 is passed over optical fiber 30 (or directly from a small light source 53 powered by power supply 22) to dichroic filter 32 in the optical probe 10, where it is redirected to the objective 19 maintained at a fixed distance above the surface 18 by the spacer 16. Light returned from the objective 19 is split by a first beam splitter 34, where a portion is directed to imaging spectrometer 24 over optical fiber 36 and another portion is directed to second beam splitter 38, which in turn divides the beam into a portion directed to camera 40 electrically connected via 42 to computer 28 and a portion coupled over the transient detector 48 electrically connected to the transient recorder 26.

The objective 19 is an optical assembly used to image the surface to be analyzed, focus the fluorescence inducing source 53 and collect the induced fluorescence signal. Since the biological contaminant could be single biological specie, the objective should be able to resolve micron size particles.

The objective 19 should meet a number of requirements, such as having a good transmission for the excitation light source and for the induced fluorescence signal. It must also be constructed so that its optical materials produce very limited or near zero auto-fluorescence. It must be relatively achromatized, meaning that its focal length has little dependency on the wavelengths.

Objectives available commercially can be based on refractive or reflective optics. There are also hybrid objectives based on both refractive and reflective optics. Another type uses diffraction, as holographic lenses, to achieve more or less the same imaging function.

It is desirable to have an objective having a medium focal length, preferably between 5 and 12 mm, but objectives with 2 to 40 mm focus distances can also achieve satisfactory results.

Another characteristic of importance for practical reasons is the need for a long working distance. This last characteristic minimizes the probability of contaminating the probe (beside the dedicated spacer) by a contact between the objective and the probed surface. A long working distance is also useful to avoid contamination if the system incorporates an automatic focus function that varies the distance between the objective and the probed surface. The numerical aperture of the objective should be chosen as high as possible to maximize the probe's light collecting ability and imaging resolution.

The materials of the objective's lenses should be chosen to minimize losses at the excitation wavelength and in the spectral band of the anticipated induced fluorescence from the diverse surfaces and compounds to be encountered. Finally, for an optimum optical design, the chosen objective should be of the infinity-corrected type. This type of objective outputs parallel light rays originating from points at the probed surface once focused, or equally said, images points from the probed surface at infinity. This characteristic greatly facilitates the insertion of subsequent optical components as beam splitters, lenses or mirrors along the optical path without affecting significantly the achievable resolution. With such an objective, the light collected from the probed surface is put in a bundle of rays that will pass through subsequent lenses or mirrors and be focused at their exact focal lengths. This also defines the imaging system magnifications as the ratio of the focus distances between the subsequent lenses/mirrors and the objective. An example of an objective that we have used and meets the different requirements is the Nikon 10×CFI LV plan EPI lens.

In order to be able to perform time-resolved spectrofluorimetry on contaminated surface, the excitation light source originating from either a source 22 situated in the electronic enclosure 12 or 53 in the optical probe 10 should be a pulsed or time modulated light source. In the described embodiment, a pulse laser is chosen but other pulsed optical sources such a light emitting diode (LED) could also be used. Because the anticipated induced fluorescence should have duration of a few nanoseconds or more, the excitation light pulse duration should be of the order of 1 nanosecond or less to produce quasi-instantaneous induced fluorescence response. To construct an ensemble composed of several tens if not hundreds of thousands of induced fluorescence spectral and time decay samples with a single sweep lasting a few seconds, the excitation light source should possess a pulse repetition frequency (PRF) of 10-100 kHz or higher.

The produced light may be coupled to an optical fiber with fiber tips located at position 53, or, if the source is sufficiently compact, having the source directly inserted at that location. The excitation light rays emitted from this position are collected by a lens and directed through the objective 19 and focused on the surface 18 to be analyzed.

The dichroic beamsplitter 32 is used to reflect and direct the excitation light through the objective while being transparent to the induced fluorescence.

The choice of the excitation light source spectrum is important as it defines the specific chromophores present in the researched contamination that will be excited and produce the fluorescent signal upon which the time-resolved spectrofluorimetry will be performed. Embodiments of the invention can also accommodate a multi-wavelength excitation light source that fires either simultaneously or sequentially light pulses containing a multiple number of wavelengths to extend the characterization of the observed surface and its contaminations by exciting a larger number of chromophores.

For a single wavelength excitation, a UV wavelength light source at around 355 nm could be used. It is well known that an excitation at this wavelength is capable of exciting NADH, a fluorescent compound present in living bacteria. The fluorescence given by the sampled compound on the surface is then spectrally and dynamically (temporally) measured giving both signatures, which can be classified, with each pulse fired by multivariate analysis. The fluorescence of NADH present in a bacterium has characteristic spectrum and time decay that occur mainly in the 400-540 nm bands. Therefore, such fluorescent response in these bands having the corresponding characteristics would indicate the presence of this class of biological contaminants on the probed surface. As an example, to further assess the class of that biological contaminant, a second light excitation at 266 nm may be fired. This wavelength is known to be able to induce a fluorescence signal from tryptophan, another substance present in bacteria. The fluorescence of tryptophan occurs in the 310-420 nm bands. This additional fluorescence response (spectrometric and dynamic) may further improve the probability of a valid classification of the contaminants. Different types of bacteria have different relative contents of NADH and tryptophan producing different signatures, which can be, used to further detail the classification results. Furthermore, there are other components in bacteria able to give fluorescent response to a UV excitation like tyrosine, phenylaniline and pyridine to name a few.

The overall fluorescence responses (spectral and dynamic) of a class of bacteria containing these multiple compounds with specific relative contents that excite at multiple wavelengths constitute the basis of a robust classification scheme.

To collect the various induced fluorescence, the collecting optics should possess a fairly good optical transmission between 300 and 700 nm. Additional dichroic filters may be added to further eliminate excitation light that may parasitize the collected fluorescence. Also, neutral filters may also be inserted along the excitation and collection optical paths to avoid contaminant bleaching or saturation of detection electronics.

Since biological materials and many other fluorescing substances of interest present good efficiencies (several percents) to produce fluorescence for a given excitation energy and that the areas of the probed surface irradiated by the UV light pulses will be fairly small (few to 50 μm in diameter) to minimize the fluorescence contribution of the background surface in comparison of micron size contaminants, the overall energy per light pulse will be fairly modest (a few tens of μJ or less).

The imaging subsystem in the optical probe 10 provides the general functionality allowing the user to inspect a selection of fluorescence images, each taken with a single pulse during the sweep. Such a system is fairly simple to implement and add basic functionalities. One of these functionalities is to allow the user to recall some of the images captured by the camera 40, tagged with the multivariate analysis of the corresponding light pulses, to inspect the shape/size of the fluorescent contaminants part of a same multivariate region of interest. It may also be used to visually inspect the analyzed surface as a classical fielded/portable microscope. The imaging subsystem is implemented by sampling with a partial mirror or a cube beamsplitter 34, 38 a part of the ray bundle coming from the surface and using a lens to image this light bundle on the camera 40 having a multi-pixel sensor, which may be a CCD, ICCD or CMOS device.

This camera 40 is connected to an electronic system (shown in FIG. 1 as part of the computer) that gathers the signals from the camera and transforms it so that it could be put to a memory module for subsequent inspection and record keeping.

The camera 40 can be used in two modes. First, it can image the induced fluorescence from the probed surface triggered by a single excitation light pulse at a fairly high repetition rate but most probably at a fraction of the one associated with excitation light pulse. The aperture duration of the camera must be sufficiently shorter than the time period between two light pulses to avoid contamination between two probed areas. The second imaging mode uses rapid white lighting pulses integrated to the optical probe to produce classic microscopy still images of the analyzed surface. These images may be recorded and/or directly send to the electronic display for live visual inspection of still images or movies of that surface.

The use of a white short-pulsed lighting eliminates imaging blurs that may result from movement of the optical probe over the inspected surface. The rapid white light pulses lighting the imaged area of the probed surface could be implemented in many ways, for example, with an electronic flash or a pulsed LED or LED arrays surrounding the objective.

For the two imaging modes (sampling imaged LIF or classical visible images), keeping the probed surface 18 within the field depth of the objective is important. This is particularly important for the analysis of structured surfaces having a certain level of roughness of having some curvature under a large magnification. This can be achieved with an autofocus function where the quality of the images produced is used as feedback information driving mechanically the vertical position of the objective. There are nowadays many optical systems that use a camera sensor and an electronic circuit to give the require commands keeping the objective lens at the right focus distance from an analyzed surface.

The spectrometer subassembly constitutes an important part of the system as it separates the wavelengths of the fluorescence induced from the probed surface. This assembly is designed with a spectral resolution between 3 and 5 nm to accommodate the usual wide fluorescence spectra (several tens of nanometers) of chromophores. It is composed of a lens focusing the collected induced fluorescence in the optical fiber tip 46. This optical fiber guides this collected fluorescence to a coupling lens of the imaging spectrometer 24. One end of that fiber is positioned at the focus of the lens of the optical probe, determining the induced fluorescent collecting field-of-view of the spectrometric subassembly, while the other end co-located with a lens adapting the f-number with the entrance imaging optics of the spectrometer.

The spectrometric subassembly magnification should be designed to have the induced fluorescence collecting field-of-view comparable or slightly larger than the UV excitation light spot produced at the focus plane of the objective and the two must be co-centered. The size of the optical fiber core, the spectrometer grating as well as the spectrometer optical design are selected to achieve the targeted spectral resolution while keeping a fairly good throughput. A multi-pixel sensor is positioned at the exit-imaging plane of the spectrometer to detect and record separately the spectrum produced by each UV excitation light pulses. This multi-pixel sensor must readout and records each fluorescence spectrum at the pulse repetition frequency (PRF) of the excitation source. This multi-pixel sensor may be a photodiode linear array, an avalanche photodiode (APD) linear array or a photomultiplier tube (PMT) linear array. If the PRF is sufficiently low, CCD, ICCD, EMCCD or CMOS 2D-detectors arrays may be used instead.

The time domain detection subassembly is another important component of the system as it gives a measurement of the time decay of the induced fluorescence from the different chromophores that have been excited by the UV excitation light source. It provides valuable dynamic signatures processed in parallel with the spectral signatures obtained simultaneously which, once combined, constitutes the individual sample of the ensemble collected during the sweep and analyzed by the multivariate technique. The time domain detection subassembly is composed of the objective 19, the partially reflective beam splitters 34 and 38, and a lens focusing the sample fluorescence on a fast optical detector 48 as a photodiode, an APD or a PMT.

An optical fiber end may also be placed at the position 48 and have the fast optical detector located at the other end of the fiber within the transient recorder 26 of the electronic enclosure 12.

As for the spectrometric subassembly, the time domain detection subassembly must be designed to have the induced fluorescence collecting field-of-view larger than the UV excitation light spot produced at the focal plane of the objective and the two must be co-centered. The anticipated time decay of biological contaminants is of the order of a few nanoseconds while other materials may show time decays much longer (microseconds and up to seconds for certain minerals). This implies that the transient recording of the fluorescence decay should have a time resolution of a nanosecond or less and collect that induced fluorescence over a time interval of 50 if not 100 ns starting at the arrival of the UV excitation pulse on the probe surface.

As the technologies associated with fast detection electronics, data transfer and computing speed progress over the next few years, it is anticipated that the spectrometric and time domain detection subassemblies described above will be combined by having each pixel of the linear array sensor at the exit imaging plane of the spectrometer collecting the time decays associated with the fluorescence measured within each resolved spectral intervals simultaneously.

Such approach is expected to improve significantly the classification power of the resulting instrument by applying the multivariate analysis on an ensemble of samples each having 2 dimensions (induced fluorescence time decay signatures for each resolved spectral intervals) instead of 1 dimension (induced fluorescence time decay for the bulk fluorescence and the spectral signature of that fluorescence).

The computer 28 is housed in the electronic enclosure and controls the different functions of the system. It controls the user interface provided by the electronic display 14, which is equipped with a touch screen and carries several of the user interface functions. The computer 28 allows configuring and controlling the excitation light source unit 22, the spectrometric subassembly, the time decay detection subassembly and the camera 40 to achieve the synchronized acquisition process during a sweep or during still image acquisitions. The computer 28 also manages the data transfers received from the spectrometric subassembly, the time decay detection subassembly and the camera as well as their recording. It controls the autofocus function of the objective based on the images provided by the camera during a sweep or during still imaging acquisitions. It performs the multivariate analysis on collected data ensembles. It records and presents the results of multivariate analysis to the user. It provides minimal library field management functions for the user. It controls the data ports 50 with external computer systems to backup the acquired data and receive library and program maintenance updates.

The computer 28 runs two main algorithms, one for the spectral domain and another for the time domain of the fluorescence signal. These are designed to process the raw data collected by the system. Each algorithm is designed with considerations based on a fluorescent signal models in both the spectral and time domains. The two dimensions are decoupled. The spectral signal is integrated over a time interval much greater than the pulse duration and the time signal is spectrally integrated. Signatures exist depending on the material for the spectral domain and the time domain. The signature in the time domain is modeled as an exponential decay. The two signatures contribute to the classification of the material at the origin of the fluorescence. For each probed surface element, the data consists in two vectors: one is a function of time and the other is a function of the wavelength. All fluorescent materials have a spectral and a time response that is characteristic of their class. The basic signal can be modeled by the following equation:

$$s(\lambda,t)=b(\lambda,t)+c(\lambda,t)$$

The fluorescent signal induced by the UV light pulse is s. b and c are the background surface and the trace contaminant fluorescing signals, respectively. With the uses of a beam splitter, system splits s in two parts more or less equals (spectrally and dynamically). The first part is directed to the time decay detection subassembly and the other part is directed to the spectrometric subassembly. During the detection process, noise is added by the detection electronics to the intrinsic photon shot noise associated with the particulate nature of light. However, it is assumed that the electronic noise is negligible in comparison of the photon shot noise. The detected spectral signal is defined as $$s(\lambda_n) = \int_{\lambda_{min}}^{\lambda_{max}} \int_0^T f_n(\lambda) s(\lambda, t) \, dt \, d\lambda$$

where $s(\lambda_n)$ is the detected spectral signal in the band n. $f_n(\lambda)$ is the sampling function of wavelength for each band and depends on the sensor spectral response characteristics. T is the duration during which the fluorescence signal is integrated by the spectrometric subassembly.

For the time signal, the problem is different since there is a time response associated with the excitation. The UV light pulse pumps molecules of the irradiated materials to an excited level. Then, these excited molecules go back to their ground (unexcited) levels after random time periods. The number of excited molecules decreases exponentially since there is no dependency between the excited materials. Since the number of excited molecules decaying in a given time interval is proportional to the total number of excited molecules, the fluorescent signal decreases following an exponential function. The dominating photon shot noise is modeled as a Poisson distribution. The acquisition system is modeled by a linear filter followed by an analog to digital converter. The resulting digitized signal is modeled using the following equation where $s_L$ described the temporal characteristics of the UV light pulse.

$$s(t_n) = \int_{t_{n-2}}^{t_n} \int_0^t \int_{\lambda_{min}}^{\lambda_{max}} h(t-\tau, \lambda) s_n(\tau) \, d\lambda \, d\tau \, dt$$

In this equation, n denotes the $n^{th}$ time interval, $\tau$ is the convolution variable and $h(t,\lambda)$ is the impulse response of the system composed of the detection electronics and of the UV light pulse dynamic shape. The output signal will be composed of a rising portion followed by a maximum and an exponential decay afterward. Since the system is linear and lowpass with a cutoff frequency higher than the frequency contained in the signal, it will follow the exponential decay of the contaminants with a delay. Therefore, the signal processing for this process consists in estimating the relaxation or time constant of a decreasing exponential buried in electronic and shot noise. The relaxation constant will provide information related to the nature of the fluorescing molecules contained in the contaminant.

The fluorescence is acquired at the same time in the spectral and time domains. Once the spectral processing has been performed and a given pixel is qualified as a spectral anomaly, the relaxation constant is estimated from the time domain fluorescence signal. The resulting relaxation constant is appended to the spectral information to further refine the classification of the fluorescing material The algorithm designed to process the spectral data acquired by is designed with the following assumptions:
1. The surface probed to acquire a single fluorescent data set (spectral and dynamic) is very small.
2. The background surface associated with each probe is the same.
3. Many probes can be acquired to assess the entire swept surface.
4. There is sufficient contrast between the fluorescence spectra of the background surface and the contaminant.

The algorithm for processing the data performs the following steps:
1. Dataset acquisition (A statistically significant number of spectral/dynamic vectors)
2. Data pre-processing (Spectral binning)
3. Data classification
   a. Background
   b. Not background
4. Background statistic computation
   a. Mean
   b. Covariance matrix
5. On all spectral vectors compute the two following detectors
   a. Anomaly detection
   b. Match filter on library of signature
   c. Outcome may be one of the following
      1. Uncontaminated
      II. Contaminated unknown
      III. Contaminated known
         i. Hazardous biological material
         ii. Hazardous organic material
         iii. Energetic material
         iv. Benign biological material
         v. Benign organic material
6. Categorization
   a. Analysis of the data for output to the reporting step
7. Reporting
   1. The dataset acquisition ensures that the collected vectors are in a sufficient number to ensure that the statistics that will be computed will be valid and represent the effective values of the statistics of the background when about half of the vectors are used if the vectors are from an uncontaminated background surface. All the vectors are tagged and their location on the probed surface is known.
   2. Data pre-processing is used to reduce the number of spectral bins in the spectral band measured by the sensor to a number that is sufficient to represent adequately the fluorescence phenomenology.
   3. Data classification provides the identification of spectral vectors that are members of the background. This identification does not need to be fully comprehensive in a first step. The complete identification of the spectral vectors associated with the background surface is done in two steps. The first step is the computation of the background vectors direction. It uses a SVD (Singular value decomposition) principal component analysis followed by a distance computation of each vector from the mean of the full set of data in the SVD space using the first two singular vectors. The second step uses a spectral angle mapper algorithm to identify all the vectors part of the background surface.
   4. Background statistics computation
      a. Mean of the background data subset.
      b. Covariance of the background data subset.
   5. Computation of detectors (performed on each acquired vectors)
      a. Anomaly detection: the anomaly detection is performed on each vectors of the dataset. The values obtained from the background vectors are used to estimate the threshold to be used to characterize a given vector as a spectral anomaly. The mathematical operator is the Square Mahalanobis distance.
      b. Match filter: the match filter computes using a library of signatures. This step is evaluated on the background vectors to evaluate the thresholds for the detectors. When a detector output is higher than the thresholds for many signatures value, the signature producing the best score above a given threshold will be selected as the potential contaminant. If the vectors only trigger an anomaly without having a sufficient score on a contaminant it will be qualified as unknown.
   6. Categorization
      a. Each vector will be processed according to the data that have been computed in the following set of categories
         1. Background
         The anomaly detector and the match filters do not have triggered in any way on these vectors.
         II. Spectral anomaly
            I. Unclassified (the material cannot be sorted in a known category): The anomaly detector result provides a value that is above the threshold for anomaly detection. However the match filters do not provide a classification level sufficient to tell what the surface giving that vector is made of.
            2. Classified
               a. Hazardous biological material
               The contaminant is reported as a biological compound that could be harmful and could be considered as a biological agent. The anomaly detector and the signature identification provide sufficient certainty to class the contaminant on the surface.
               b. Hazardous organic material
               The contaminant on the surface is organic in nature and can be toxic or dangerous. The quantity of material may be insufficient to be dangerous. However, the probed surface has been in contact with a dangerous material organic in nature. The anomaly detector and the signature identification provide sufficient certainty to class the contaminant on the surface.

c. Energetic material

The contaminant on the surface is reported as an explosive or a precursor of an explosive. The quantity may not be sufficient to show any risk. The anomaly detector and the signature identification provide sufficient certainty to class the contaminant on the surface.

d. Benign biological material

The contaminant is reported as a benign biological material. The anomaly detector and the signature identification provide sufficient certainty to class the contaminant on the surface.

e. Benign organic material

The contaminant is reported as organic, but not dangerous. The anomaly detector and the signature identification provide sufficient certainty to class the contaminant on the surface.

7. Reporting

The report for the probed surface includes the swept area, its location on the surface if it is possible and the proportions of vectors identified as background spectral anomaly, as classified biological and as classified non biological material. Based on these information and the amplitudes of the collected signals, an evaluation of the quantity of contaminants per surface area is derived.

Figure 2:
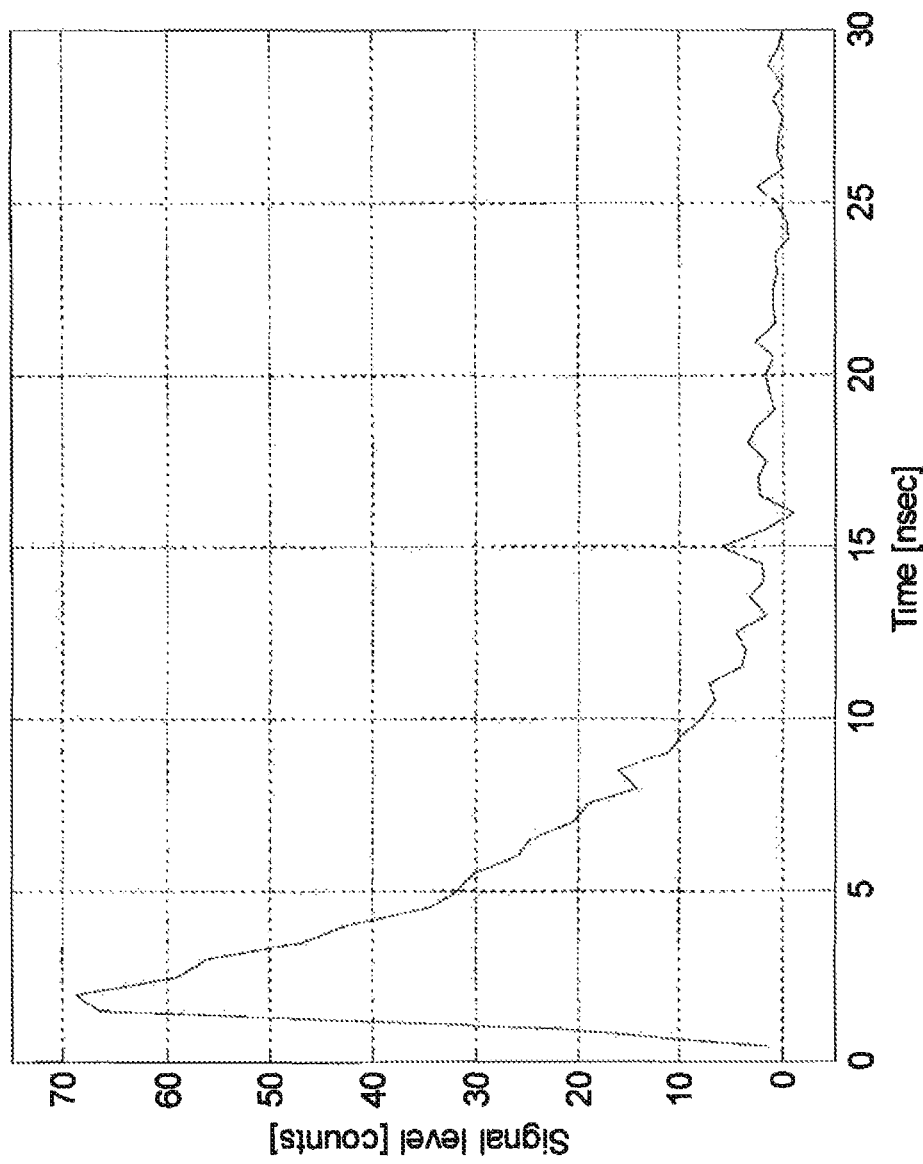
FIG. 2 is an example of an exponential transient decay associated with induced fluorescence.

For each time decay vectors, four signal zones are identified: the rise, the transition, the relaxation or decrease, and, the low signal zone. The relaxation zone contains the information about the fluorescence time decay, which can be derived from the slope of the logarithm of the amplitude in that portion of the signal. In the rise and transition zones, the induced fluorescence reacts to the UV light pulse shape and the linear signal processing acquisition system. If only the relaxation portion is used, assuming there is no excitation at that time and the acquisition system is fast enough to react to the decreasing exponential, the only remaining contribution to the signal time decay is defined by this logarithmic slope. As a result, the information is simple to extract in that signal zone. In the last signal zone, the information content is such that noise overwhelms it and including it in the process will decrease the accuracy of the relaxation time derivation. FIG. 2 shows an example of a transient fluorescent signal. The first section where the signal is rising is from 0 to about 2 ns. The signal then decreases slowly until approximately 14 ns. After 14 ns, instrument noise prevails as shown in FIG. 2.

The process designed to extract the relaxation constant of the fluorescence should contain the following components:

1. Determination of the beginning of the exponential decay zone;
2. Determination of the useful signal zone;
3. Estimation of the amplitude of the exponential decay;
4. Estimation of the relaxation constant.

The beginning of the decay zone starts when there are no more excitations provided by the incident light pulse and after a time interval related to the response time of the detection electronics. The knowledge of the UV pulse duration and of the bandwidth of the detection electronics will contribute in determining the time delay before entering the decay zone. Assuming the detection electronic response is negligible in comparison of the UV pulse duration, the first sample of the decay zone should be located at least at two-pulse width of the peak of the collected signal. This peak is the maximum of the fluorescence time function.

As the time from the beginning of the decay zone increases, the signal to noise ratio decreases. At some point, there will be no increase in information by adding one more data value. Adding points beyond that point will diminish the quality of the estimation. The determination of this last exploitable sample is performed with the use of the peak value. The choice is made using the following procedure.

1) Estimate the noise of the instrumentation using points that are very far from the location where the signal is located;
2) Multiply by 2 this value and set it as the threshold;
3) As the signal decays, detect the first point that is below that threshold;
4) The last point included in the set of points for the estimation of the time constant is the point before the one detected in 3;
5) If there is no such point then use the first two points after the peak value.

Two parameters have to be estimated. The more important is the time constant which is the rate at which the fluorescence is decaying. The second is the amplitude of the exponential. Two methods for this estimation can be used. The first method is based on the LMS (Least Mean Square) criterion in which the sum of the squares of the errors is minimized as a function of the two required parameters. This method yields the following equations.

$$A = \exp\left[\frac{\sum \ln(s(t_n))\sum t_n^2 - \sum t_n - N\sum t_n \ln(s(t_n))}{N\sum t_n^2 - (\sum t_n)^2}\right]$$

$$\alpha = \frac{\sum \ln(s(t_n))\sum t_n - N\sum t_n \ln(s(t_n))}{N\sum t_n^2 - (\sum t_n)^2}$$

Another way of estimating the parameters is based on the maximum likelihood technique, where the likelihood of a value is maximized. In this last case, the method requires the assumption of a probability distribution to represent the likelihood. To provide the estimators, the Poisson distribution is used because it is the model for shot noise, which is the major contribution in the signal.

The following equations are used as the basis of the computation. Since these two equations cannot be solved directly, minimization techniques or zero finding iterative methods are used. The amplitude of the exponential requires the estimation of the time decay.

For the maximum likelihood estimation, the estimators are given by $$\frac{\sum t_n \exp(-\alpha t_n)}{\sum \exp(-\alpha t_n)} = \frac{\sum t_n s(t_n)}{\sum s(t_n)} \text{ and}$$

$$A = \frac{\sum s(t_n)}{\sum \exp(-\alpha t_n)}$$

The extraction of the time decay constant from the maximum likelihood estimation is performed using a least square error, or finding the zero of the following function:

$$F(\alpha) \frac{\sum t_n \exp(-\alpha t_n)}{\sum \exp(-\alpha t_n)} - \frac{\sum t_n s(t_n)}{\sum s(t_n)} \text{ or}$$

$$\alpha : \min\left[\left(\frac{\sum t_n \exp(-\alpha t_n)}{\sum \exp(-\alpha t_n)} - \frac{\sum t_n s(t_n)}{\sum s(t_n)}\right)^2\right]$$

This process is performed for each pixel where fluorescence is detected. The estimated relaxation constant is appended to the spectral fluorescence information.

It will thus be seen that embodiments of the invention provide a convenient tool for first responders to recognize the presence of potentially hazardous substances, which is rapid and portable.

The invention claimed is:

1. A man portable device for detecting the presence of hazardous material, comprising:
 a pulsed or time-modulated light source;
 an objective scannable across a surface of a sample for projecting light from the light source onto a succession of spots on the surface of the sample to induce fluorescence;
 a spectrometer for performing a spectral analysis of the induced fluorescence to create a first dataset defining a first vector as a function of wavelength;
 a time domain detector for measuring the time decay of the induced fluorescence to create a second dataset defining a second vector as a function of time; and
 a computer configured to identify hazardous material by performing independent multivariate analysis on the first and second vectors as the objective is scanned across the sample surface based on fluorescent signal models for hazardous materials in the spectral and time domains.

2. A man portable device as claimed in claim 1, wherein the computer is configured to compare the results of the multivariate analysts with a library of spectral and temporal characteristics of products of interest.

3. A man portable device as claimed in claim 1 further comprising a spacer for maintaining the objective a fixed distance from the sample surface.

4. A man portable device as claimed in claim 3, wherein the spacer comprises a ball bearing arrangement.

5. A man portable device as claimed in claim 1 further comprising an optical demultiplexer for separating the induced fluorescence returned from the sample into a first portion directed to the spectrometer and a second portion directed to the time domain detector.

6. A man portable device as claimed in claim 5, further comprising a camera for receiving a portion of light returned from the sample that is configured to image the induced fluorescence from the probed surface triggered by a single excitation light pulse or produce microscopy still images of the sample.

7. A man portable device as claimed in claim 5, wherein the optical demultiplexer includes a dichroic filter to eliminate excitation light that could parasitize the induced fluorescence.

8. A man portable device as claimed in claim 5, wherein the optical multiplexer is mounted in a pen-like probe including a touch screen display for user input/output.

9. A man portable device as claimed in claim 8, further comprising a backpack containing an electronics enclosure coupled to the pen-like probe by optical fibers and low power electrical cables.

10. A man portable device as claimed in claim 1, wherein the spots defined by the excitation light range from few to 50 microns in size.

11. A man portable device as claimed in claim 1, wherein the objective has a focal length between 5 to 12 mm and is of the infinity corrected type.

12. A man portable device as claimed in claim 1, wherein the light source is pulsed with a duration of a few nanosecond or less and has a frequency of at least 10 kHz.

13. A man portable device as claimed in claim 1, wherein the light source is a multi-wavelength excitation source.

14. A man portable device as claimed in claim 1, wherein the light source is a light source with an excitation wavelength around 355 nm.

15. A man portable device as claimed in claim 14, wherein the light source has a second excitation wavelength around 266 nm.

16. A man portable device as claimed in claim 14, wherein the time domain detector has a time resolution of 1 ns or less and collects the induced fluorescence over a time period of at least 50 ns.

17. A man portable device as claimed in claim 1, wherein the computer is programmed to integrate a spectral signal from the spectrometer over a time period greater than the fluorescence pulse duration and spectrally integrate a time signal derived from the time domain detector.

18. A man portable device as claimed in claim 17, wherein signatures of products in the time domain are modeled as an exponential time decay vectors.

19. A man portable device as claimed in claim 18, wherein for each time decay vector the computer is configured to identify four signal zones, namely a rise, transition, relaxation, and a low signal zone.

20. A computer-implemented method of detecting the presence of hazardous material, comprising:
 scanning a pulsed or time-modulated light source across a surface of a sample onto a succession of spots on the surface of the sample to induce fluorescence;
 performing a spectral analysis of the induced fluorescence to create a first dataset defining a first vector as a function of wavelength;
 measuring the time decay of the induced fluorescence to create a second dataset defining a second vector as a function of time; and
 identifying hazardous material by performing independent multivariate analysis on the first and second vectors as the objective is scanned across the sample surface based on fluorescent signal models for hazardous materials in the spectral and time domains.

21. A method as claimed in claim 20, further comprising comparing the results of the multivariate analysts with a library of spectral and temporal characteristics of products of interest.

22. A method as claimed in claim 20, wherein an objective scanning the surface is maintained a fixed distance from the sample surface during scanning.

23. A method as claimed in claim 20 further comprising separating the induced fluorescence returned from the sample into a first portion directed to a spectrometer and a second portion directed to a time domain detector simultaneously.

24. A method as claimed in claim 23, wherein a third portion of the induced fluorescence is directed to a camera to capture an image of the sample surface.

25. A method as claimed in claim 20, wherein the spots defined by the excitation light range from few to 50 microns in size and the light source is pulsed with a duration of a few nanosecond or less.

26. A method as claimed in claim 25, wherein the pulsed light source has a frequency of at least 10 kHz.

27. A method as claimed in claim 20, wherein the sample is excited with a multi-wavelength excitation source.

28. A man portable device as claimed in claim 20, wherein the time domain detector has a time resolution of 1 ns or less and collects the induced fluorescence over a time period of at least 50 ns.

29. A man portable device as claimed in claim 20, wherein a spectral signal from the spectrometer is integrated over a time period greater than the fluorescence pulse duration and a time signal derived from the time domain detector is spectrally integrated and signatures of products in the time domain are modeled as an exponential time decay vectors.

* * * * *